(12) United States Patent
Stark et al.

(10) Patent No.: US 10,034,946 B2
(45) Date of Patent: *Jul. 31, 2018

(54) ODOR FREE MILK PRODUCTION ENHANCERS FOR RUMINANTS

(71) Applicant: ZINPRO CORPORATION, Eden Prairie, MN (US)

(72) Inventors: Peter A. Stark, Inver Grove Heights, MN (US); Cory Shawn Kending, Champlin, MN (US); Michael Thomas Socha, Rogers, MN (US)

(73) Assignee: Zinpro Corporation, Eden Prairie, MN (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/805,571

(22) Filed: Jul. 22, 2015

(65) Prior Publication Data

US 2017/0020830 A1 Jan. 26, 2017

(51) Int. Cl.

| | |
|---|---|
| *A23K 20/10* | (2016.01) |
| *A23K 50/10* | (2016.01) |
| *A23K 50/75* | (2016.01) |
| *A23K 50/30* | (2016.01) |
| *A61K 47/48* | (2006.01) |
| *A23K 40/10* | (2016.01) |
| *A23K 20/105* | (2016.01) |
| *A23K 20/158* | (2016.01) |
| *A23K 20/20* | (2016.01) |

(52) U.S. Cl.
CPC ...... *A61K 47/48176* (2013.01); *A23K 20/105* (2016.05); *A23K 20/158* (2016.05); *A23K 20/30* (2016.05); *A23K 40/10* (2016.05); *A23K 50/10* (2016.05)

(58) Field of Classification Search
CPC ............................ B01J 20/226; B01J 31/1691
See application file for complete search history.

(56) References Cited

U.S. PATENT DOCUMENTS

| | | | | |
|---|---|---|---|---|
| 2,694,683 A | * | 11/1954 | Morway et al. | C10M 5/00 508/216 |
| 4,055,667 A | * | 10/1977 | Linton | A23K 1/006 426/62 |
| 4,153,735 A | * | 5/1979 | Mommer | A23K 20/10 426/2 |
| 4,333,923 A | * | 6/1982 | Beck | A23K 1/1618 424/115 |
| 4,376,790 A | | 3/1983 | Ames | |
| 4,804,547 A | | 2/1989 | Vanderbilt et al. | |
| 2005/0084474 A1 | * | 4/2005 | Wu | A61L 9/014 424/76.1 |

FOREIGN PATENT DOCUMENTS

| | | | | |
|---|---|---|---|---|
| EP | 1474997 A1 | * | 11/2004 | ............. A23K 40/10 |
| WO | 8400669 A1 | | 3/1984 | |
| WO | 91/11915 A1 | | 8/1991 | |
| WO | WO 9111915 A1 | * | 8/1991 | ............. A23K 1/003 |
| WO | 2014047497 A1 | | 3/2014 | |

OTHER PUBLICATIONS

Complex Soap Greases, Rizvi, A Comprehensive Review of Lubricant Chemistry, ASTM International (2009) pp. 456-459.*
Andries, J. I., et al., "Isoacids in Ruminant Nutrition: Their Role in Ruminal and Intermediary Metabolism and Possible Influences on Performances—A Review", Animal Feed Science and Technology, vol. 18 (1987), pp. 169-180. Mar. 17, 1987.
ZINPRO Corporation, PCT/US2016/043494 filed Jul. 22, 2016, "The International Search Report and The Written Opinion of the International Searching Authority" dated Sep. 27, 2016.

* cited by examiner

*Primary Examiner* — Bethany P Barham
*Assistant Examiner* — Lisbeth C. Robinson
(74) *Attorney, Agent, or Firm* — McKee, Voorhees & Sease, PLC

(57) ABSTRACT

A feed supplement for ruminants to increase milk production, comprised of a carrier and the reaction product of a water soluble polycarboxylic acid, a metal salt, and a C3 to C10 fatty acid, the water soluble carboxylic acid having a pendant carboxylic acid group and being linked to the metal of the metal salt, which is in turn linked to the C3 to C10 fatty acid.

6 Claims, No Drawings

ODOR FREE MILK PRODUCTION ENHANCERS FOR RUMINANTS

FIELD OF THE INVENTION

Production and use of essentially odor free nutrients for ruminal bacteria leading to increased milk production.

BACKGROUND OF THE INVENTION

It is well-known in the animal nutrition field that volatile fatty acids such as butyric acid, isobutyric acid, and valeric acid improve milk production in dairy cows. However one of the main drawbacks of using these volatile acids for this purpose is their strong odor. The odor has sometimes been described as smelling of extreme rancidity, vomit, and/or extreme body odor. Eastman Kodak originally produced these compounds for the animal industry, see U.S. Pat. No. 4,804,547, which discloses making calcium salts of the isoacids, but they never saw widespread use, due to their odor. The odor was less a problem to the animals eating the fermentation enhancer than it was to the workers producing it. Oftentimes workers could not stand the smell, sickened and some even claimed adverse medical effects. There were some efforts to decrease odor, such as U.S. Pat. No. 4,376,790, which relates to decreasing odor by making ammonium salts of the isoacids. Another attempt at improving this type of product was to make the imines from urea and corresponding acid aldehydes (see Publication No. WO 84/006769). However, the aldehydes are significantly more expensive than the acids and this therefore never became a viable product.

Isoacids is the collective term for the branched-chain fatty acids: isobutyric, 2-methylbutyric and isovaleric acid and the straight-chain valeric acid, which are naturally produced in ruminant's digestive tracts. They are mainly built up from the degradation products of the amino acids valine, isoleucine, leucine and proline and should in turn be used for the biosynthesis of those amino acids and higher branched chain volatile fatty acids. Besides their role as specific nutrients for the ruminal cellulolytic bacteria, isoacids seem to have a general positive influence on microbial fermentation. Only limited information is available on the influence of isoacids on the intermediary metabolism. Alteration of the growth hormone and indirect effects (via amino acids) on mammary gland and skeletal muscles are suggested. From a review of cattle experiments, a nutritional supplement of isoacids may also has a positive influence on milk production. For a scientific discussion of isoacids in the digestion and metabolism of the ruminant, see *Animal Feed Science and Technology*, 18 (1987) 169-180.

There is a continuing need for a convenient low-cost process to lower the odor so as to make volatile fatty acid derived fermentation enhancers a viable feed supplement product that can be used to increase milk production.

There are additional phenomena that are taken advantage in the present invention besides odor reduction. For example, sugars are known to have energy value in feeding ruminants. Typically, they are sticky and difficult to work with. Often they are delivered in liquid form. This invention can provide in some embodiments those as part of the fermentation enhancer composition in an easily processable, and dosable form.

In addition, macro minerals such as calcium and magnesium are important to both the microflora of the rumen, as well as the overall wellbeing of the animal.

There is therefore also a continuing need to develop an odor free fermentation enhancer to supplement ruminant feed that combines all three of these features to alleviate several problems associated with these feed ingredients in the past, all to make a viable product that can be used to increase milk production.

This invention has as its primary objective fulfillment of this continuing need.

SUMMARY OF THE INVENTION

This invention overcomes the odor problems of volatile fatty acid milk enhancers, and combines the advantages of processable sugars and macro minerals such as, calcium and magnesium, by preparing feed supplements for ruminants from polycarboxylic acid metal salts and volatile fatty acids. Preferably, calcium and magnesium salts of pendant polycarboxylic acid groups derived from readily available materials, such as pectin are reacted with the volatile fatty to provide useful low odor ruminant milk enhancers.

DETAILED DESCRIPTION OF THE PREFERRED EMBODIMENTS

The feed supplements that are essentially odor free and that enhance milk production are prepared by reacting a water soluble polycarboxylic acid, metal salt with pendant carboxylic acid groups and a C3 to C10 fatty acid. The preferred C3 to C10 fatty acids are isoacids selected from the group consisting of isobutyric, isovaleric, 2-methyl-butyric and valeric acid. The preferred pendant carboxylic acid or polyacid groups come from polyacrylic acid, pectin, alginic acid and various molecular weight forms of carboxymethylcellulose (cmc).

The metal ions are preferably selected from the group consisting of calcium, magnesium, zinc, manganese, copper and iron, but are most preferably calcium or magnesium.

The product may be dosed to the ruminant animals at from 10 grams per head to 100 grams per head, preferably from 20 grams per head to 80 grams per head per day.

As illustrated in the examples below, the composition may be used on a dry as is basis (neat), or with the usual carriers or feed supplements such as corn cobs, whey, fermentation byproducts, soybean flour, soy meal, and barley, etc. It can also be used directly as a liquid.

The following examples of preparation are shown to illustrate in an exemplary fashion various isoacids, various carriers, various metals, particularly calcium and magnesium, and examples of some product neat (without carrier and some products with carrier). In addition, the polymers used illustrate pectin, alginic acid, polyacrylic acid, and carboxymethylcellulose. The four volatile fatty acids used will be butyric, isobutyric, valeric and, 2-methyl-butyric acid. The structures illustrated are functionally shown below:

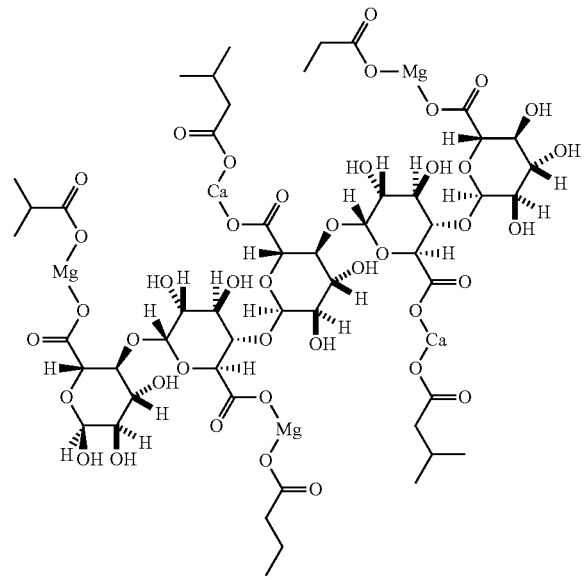

(pectin metal salt with volatile fatty acids (VFA))

For this first series of examples, i.e., 1 through 80, the only testing done on the samples was an odor test to show how this synthesis produces a reaction product of low odor. The odor testing was done blind, according to the following methodology.

Odor Testing Protocol:
The Odor Assessor:
 1. Must be free of colds or physical conditions that may affect the sense of smell;
 2. Must not chew gum or eat at least 30 minutes prior to the test;
 3. Must refrain from eating spicy foods prior to the test; and
 4. Must not wear perfume cologne or after shave the day of the test.

The Odor Intensity Test:
During an odor test, the odor assessor, sniffs a sample of the product as the container is opened approximately six inches directly below the assessor's nostrils. The odor intensity is then qualitatively compared to control samples; isobutyric acid (IBA), 1:10 IBA/water, 1:100 IBA/water and pure water. A score of zero odor units indicates no smell. A score of three odor units indicates an odor intensity equivalent to 1:100 IBA/water. A score of six odor units indicates an odor intensity equivalent to 1:10 IBA/water. A score of ten odor units indicates an odor as intense as undiluted isobutyric acid. The test is repeated as necessary with the assessor revisiting the controls and test product as often as necessary prior to a qualitative confidence being reached. The assessor then repeats this test on a series of no greater than ten individual test products in one 24 hour period. The individual estimated intensities for three to five assessments and are averaged to the nearest whole number to determine the reportable odor intensity. Some of the Examples are of ingredients other than the invention to provide very smelly comparisons or controls. These are indicated as (comparative).

Example 1

$MgCl_2$-Mixed VFA-Pectin-NaOH
Pectin (10.02 g, 51 mmols), was suspended in 100 mL of 2M NaOH (8.01 g, 0.2 mols) and heated to 70° C. for 4 hours. Isobutyric Acid (1.39 g, 15.8 mmols), Isovaleric Acid (1.01 g, 9.89 mmols), 2-MethylButyric Acid (1.41 g, 12.9 mmols) and Valeric Acid (1.27 g, 12.4 mmols) were added in one portion and after 10 minutes of stirring Magnesium Chloride Hexahydrate (10.38 g, 51 mmols) in 5 mL of water was slowly added to the resulting reddish orange suspension. After stirring for an additional hour to ensure homogeneity the burnt red suspension was dried in a vacuum oven and analyzed for smell.
Smell Factor: 2

Example 2

$MgCl_2$-Mixed VFA-Pectin-NaOH-Corn Cob
Pectin (10.00 g, 51 mmols), was suspended in 100 mL of 2M NaOH (7.98 g, 0.2 mols) and heated to 70° C. for 4 hours. Isobutyric Acid (1.41 g, 15.8 mmols), Isovaleric Acid (1.00 g, 9.89 mmols), 2-MethylButyric Acid (1.31 g, 12.9 mmols) and Valeric Acid (1.27 g, 12.4 mmols) were added in one portion and after 10 minutes of stirring Magnesium Chloride Hexahydrate (10.35 g, 51 mmols) in 5 mL of water was slowly added to the resulting reddish orange suspension. After stirring for an additional hour to ensure homogeneity the burnt red suspension was added to 33 g of Ground Corn Cob and dried in a vacuum oven prior to smell analysis.
Smell Factor: 1

Example 3

$MgCl_2$-Isobutyric Acid-CMC High Viscosity-KOH-Corn Cob
Sodium Carboxymethyl Cellulose-High Viscosity (2.00 g, ~7.27 mmols of COOH) was dissolved in 100 mL of 2M KOH (11.21 g, 0.2 mols) over 4 hours. To this was added Isobutyric Acid (0.67 mL, 7.27 mmols) and the resulting suspension was stirred for 20 minutes and to this was added Magnesium Chloride Hexahydrate (1.48 g, 7.27 mmols). The homogenous suspension was then stirred for an additional hour, added to 33 g of Ground Corn Cob and dried in a vacuum oven prior to analyzing for smell.
Smell Factor: 1

Example 4

$MgCl_2$-Isobutyric Acid-CMC-High Viscosity-KOH
Sodium Carboxymethyl Cellulose-High Viscosity (2.03 g, ~7.27 mmols of COOH) was dissolved in 100 mL of 2M KOH (11.20 g, 0.2 mols) over 4 hours. To this was added Isobutyric Acid (0.67 mL, 7.27 mmols) and the resulting suspension was stirred for 20 minutes and to this was added Magnesium Chloride Hexahydrate (1.50 g, 7.27 mmols). The homogenous suspension was then stirred for an additional hour, evaporated and dried completely in a vacuum oven.
Smell Factor: 1

Example 5

MgCl$_2$-Valeric/IsoValeric-CMC High Viscosity-KOH-Corn Cob

Sodium Carboxymethyl Cellulose-High Viscosity (1.96 g, ~7.27 mmols of COOH) was dissolved in 100 mL of 2M KOH (11.18 g, 0.2 mols) over 4 hours. To this was added both Valeric Acid (0.39 mL, 3.64 mmols) and Isovaleric Acid (0.39 mL, 3.64 mmols) the resulting suspension was stirred for 20 minutes and to this was added Magnesium Chloride Hexahydrate (1.49 g, 7.27 mmols). The homogenous suspension was then stirred for an additional hour, added to 33 g of Ground Corn Cob and dried in a vacuum oven prior to analyzing for smell.

Smell Factor: 1

Example 6

MgCl$_2$-Valeric/IsoValeric-CMC High Viscosity-KOH

Sodium Carboxymethyl Cellulose-High Viscosity (1.99 g, ~7.27 mmols of COOH) was dissolved in 100 mL of 2M KOH (11.20 g, 0.2 mols) over 4 hours. To this was added both Valeric Acid (0.39 mL, 3.64 mmols) and Isovaleric Acid (0.39 mL, 3.64 mmols) the resulting suspension was stirred for 20 minutes and to this was added Magnesium Chloride Hexahydrate (1.45 g, 7.27 mmols). The homogenous suspension was then stirred for an additional hour, evaporated and dried completely in a vacuum oven.

Smell Factor: 1

Example 7

MgCl$_2$-Valeric/IsoValeric/2-Methyl Butyric-CMC High Viscosity-KOH-Corn Cob

Sodium Carboxymethyl Cellulose-High Viscosity (1.97 g, ~7.27 mmols of COOH) was dissolved in 100 mL of 2M KOH (11.21 g, 0.2 mols) over 4 hours. To this was added Valeric Acid (0.27 mL, 2.42 mmols), Isovaleric Acid (0.27 mL, 2.42 mmols) and 2-methyl butyric acid (0.27 mL, 2.42 mmols) the resulting suspension was stirred for 20 minutes and to this was added Magnesium Chloride Hexahydrate (1.50 g, 7.27 mmols). The homogenous suspension was then stirred for an additional hour, added to 33 g of Ground Corn Cob and dried in a vacuum oven prior to analyzing for smell.

Smell Factor: 1

Example 8

MgCl$_2$-Valeric/IsoValeric/2-Methyl Butyric-CMC High Viscosity-KOH

Sodium Carboxymethyl Cellulose-High Viscosity (1.96 g, ~7.27 mmols of COOH) was dissolved in 100 mL of 2M KOH (11.18 g, 0.2 mols) over 4 hours. To this was added Valeric Acid (0.27 mL, 2.42 mmols), Isovaleric Acid (0.27 mL, 2.42 mmols) and 2-methyl butyric acid (0.27 mL, 2.42 mmols) the resulting suspension was stirred for 20 minutes and to this was added Magnesium Chloride Hexahydrate (1.49 g, 7.27 mmols). The homogenous suspension was then stirred for an additional hour, evaporated and dried completely in a vacuum oven.

Smell Factor: 1

Example 9

MgCl$_2$-2-Methyl Butyric Acid-Polyacrylic Acid-KOH

Polyacrylic Acid (50% solution, 7.61 g, 51 mmols), was dissolved in 50 mL of 2M KOH (5.56 g, 0.1 mols). 2-methyl butyric acid (5.63 mL, 51 mmols) was added which was followed by the dropwise addition of Magnesium Chloride Hexahydrate (10.31 g, 51 mmol) dissolved in 5 mL of water. The resulting white suspension was stirred for an additional hour until homogenous, dried in a vacuum oven and analyzed for smell.

Smell Factor: 1

Example 10

MgCl$_2$-2-Methyl Butyric Acid-Polyacrylic Acid-KOH-Corn Cob

Polyacrylic Acid (50% solution, 7.55 g, 51 mmols), was dissolved in 50 mL of 2M KOH (5.57 g, 0.1 mols). 2-methyl butyric acid (5.63 mL, 51 mmols) was added which was followed by the dropwise addition of Magnesium Chloride Hexahydrate (10.38 g, 51 mmol) dissolved in 5 mL of water. The resulting white suspension was stirred for an additional hour until homogenous, added to 17 g of Ground Corn Cob and dried in the vacuum oven prior to smell analysis.

Smell Factor: 2

Example 11

MgCl$_2$-Isobutyric/2-Methyl Butyric Acid-Polyacrylic Acid-KOH

Polyacrylic Acid (50% solution, 7.56 g, 51 mmols), was dissolved in 50 mL of 2M KOH (5.57 g, 0.1 mols). Isobutyric (2.37 mL, 25.5 mmols) and 2-methyl butyric acid (2.82 g, 25.5 mmols) were added which was followed by the dropwise addition of Magnesium Chloride Hexahydrate (10.30 g, 51 mmol) dissolved in 5 mL of water. The resulting white suspension was stirred for an additional hour until homogenous, dried in a vacuum oven and analyzed for smell.

Smell Factor: 1

Example 12

MgCl$_2$-Isobutyric/2-Methyl Butyric Acid-Polyacrylic Acid-KOH-Corn Cob

Polyacrylic Acid (50% solution, 7.53 g, 51 mmols), was dissolved in 50 mL of 2M KOH (5.55 g, 0.1 mols). Isobutyric (2.37 mL, 25.5 mmols) and 2-methyl butyric acid (2.82 g, 25.5 mmols) were added which was followed by the dropwise addition of Magnesium Chloride Hexahydrate (10.36 g, 51 mmol) dissolved in 5 mL of water. The resulting white suspension was stirred for an additional hour until homogenous, added to 17 g of Ground Corn Cob and dried in the vacuum oven prior to smell analysis.

Smell Factor: 2

Example 13

MgCl$_2$-Isobutyric/Valeric/IsoValeric Acid-Polyacrylic Acid-KOH

Polyacrylic Acid (50% solution, 7.50 g, 51 mmols), was dissolved in 50 mL of 2M KOH (5.60 g, 0.1 mols). Isobutyric (1.58 mL, 17 mmols), Valeric (1.86 mL, 17 mmols) and Isovaleric (1.87 mL, 17 mmols) were added which was followed by the dropwise addition of Magnesium Chloride Hexahydrate (10.37 g, 51 mmol) dissolved in 5 mL of water. The resulting white suspension was stirred for an additional hour until homogenous, dried in a vacuum oven and analyzed for smell.

Smell Factor: 1

Example 14

MgCl$_2$-Isobutyric/Valeric/IsoValeric Acid-Polyacrylic Acid-KOH-Corn Cob

Polyacrylic Acid (50% solution, 7.55 g, 51 mmols), was dissolved in 50 mL of 2M KOH (5.59 g, 0.1 mols). Isobutyric (1.58 mL, 17 mmols), Valeric (1.86 mL, 17 mmols) and Isovaleric (1.87 mL, 17 mmols) were added which was followed by the dropwise addition of Magnesium Chloride Hexahydrate (10.33 g, 51 mmol) dissolved in 5 mL of water. The resulting white suspension was stirred for an additional hour until homogenous, added to 17 g of Ground Corn Cob and dried in the vacuum oven prior to smell analysis.

Smell Factor: 2

Example 15

MgCl$_2$-Isobutyric Acid-Pectin-KOH

Pectin (10.01 g, 51 mmols), was suspended in 100 mL of 2M KOH (11.17 g, 0.2 mol) and heated to 70° C. for 4 hours. Isobutyric Acid (4.73 mL, 51 mmols) was added in one portion and after 10 minutes of stirring Magnesium Chloride Hexahydrate (10.35 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 1

Example 16

MgCl$_2$-Isobutyric Acid-Pectin-KOH-Corn Cob

Pectin (9.97 g, 51 mmols), was suspended in 100 mL of 2M KOH (11.19 g, 0.2 mol) and heated to 70° C. for 4 hours. Isobutyric Acid (4.73 mL, 51 mmols) was added in one portion and after 10 minutes of stirring Magnesium Chloride Hexahydrate (10.40 g, 51 mmols) in 5 mL of water was slowly added to the resulting reddish orange suspension. After stirring for an additional hour to ensure homogeneity the burnt red suspension was added to 33 g of Ground Corn Cob and dried in a vacuum oven prior to smell analysis.

Smell Factor: 1

Example 17

MgCl$_2$-Valeric/Isovaleric Acid-Pectin-KOH

Pectin (10.00 g, 51 mmols), was suspended in 100 mL of 2M KOH (11.15 g, 0.2 mol) and heated to 70° C. for 4 hours. Valeric (2.78 mL, 25.5 mmols) and Isovaleric (2.81 mL, 25.5 mmols) were both added in one portion and after 10 minutes of stirring Magnesium Chloride Hexahydrate (10.39 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 1

Example 18

MgCl$_2$-Valeric/Isovaleric Acid-Pectin-KOH-Corn Cob

Pectin (10.03 g, 51 mmols), was suspended in 100 mL of 2M KOH (11.21 g, 0.2 mol) and heated to 70° C. for 4 hours. Valeric (2.78 mL, 25.5 mmols) and Isovaleric (2.81 mL, 25.5 mmols) were both added in one portion and after 10 minutes of stirring Magnesium Chloride Hexahydrate (10.37 g, 51 mmols) in 5 mL of water was slowly added to the resulting reddish orange suspension. After stirring for an additional hour to ensure homogeneity the burnt red suspension was added to 33 g of Ground Corn Cob and dried in a vacuum oven prior to smell analysis.

Smell Factor: 1

Example 19

MgCl$_2$-Isobutyric/Isovaleric/2-Methyl-Butyric Acid-Pectin-KOH

Pectin (9.95 g, 51 mmols), was suspended in 100 mL of 2M KOH (11.15 g, 0.2 mol) and heated to 70° C. for 4 hours. Isobutyric (1.58 mL, 17 mmols), Isovaleric (1.87 mL, 17 mmols) and 2-methyl butyric (1.88 mL) were added in one portion and after 10 minutes of stirring Magnesium Chloride Hexahydrate (10.34 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 1

Example 20

MgCl$_2$-Isobutyric/Isovaleric/2-Methyl-Butyric Acid-Pectin-KOH-Corn Cob

Pectin (10.02 g, 51 mmols), was suspended in 100 mL of 2M KOH (11.25 g, 0.2 mol) and heated to 70° C. for 4 hours. Isobutyric (1.58 mL, 17 mmols), Isovaleric (1.87 mL, 17 mmols) and 2-methyl butyric (1.88 mL, 17 mmols) were added in one portion and after 10 minutes of stirring Magnesium Chloride Hexahydrate (10.33 g, 51 mmols) in 5 mL of water was slowly added to the resulting reddish orange suspension. After stirring for an additional hour to ensure homogeneity the burnt red suspension was added to 33 g of Ground Corn Cob and dried in a vacuum oven prior to smell analysis.

Smell Factor: 1

Example 21

MgCl$_2$-Mixed VFA-CMC (Sodium Salt)-High Viscosity

Sodium Carboxymethyl Cellulose-High Viscosity (2.01 g, ~7.27 mmols of COOH) was dissolved in 100 mL of H$_2$O over 24 hours. To this was added Isobutyric Acid (198.5 mg, 2.25 mmols), Isovaleric Acid (144.2 mg, 1.41 mmols), 2-MethylButyric Acid (187.4 mg, 1.83 mmols) and Valeric Acid (181.4 mg, 1.77 mmols) the resulting suspension was stirred for 20 minutes and to this was added Magnesium Chloride Hexahydrate (1.45 g, 7.27 mmols). The homogenous suspension was then stirred for an additional hour, dried in the vacuum oven and analyzed for smell.

Smell Factor: 1

Example 22

MgCl$_2$-Mixed VFA-CMC (Sodium Salt)-High Viscosity-Corn Cob

Sodium Carboxymethyl Cellulose-High Viscosity (1.97 g, ~7.27 mmols of COOH) was dissolved in 100 mL of H$_2$O over 24 hours. To this was added Isobutyric Acid (198.5 mg, 2.25 mmols), Isovaleric Acid (144.2 mg, 1.41 mmols), 2-MethylButyric Acid (187.4 mg, 1.83 mmols) and Valeric Acid (181.4 mg, 1.77 mmols) the resulting suspension was stirred for 20 minutes and to this was added Magnesium Chloride Hexahydrate (1.47 g, 7.27 mmols). The homogenous suspension was then stirred for an additional hour, dried in the vacuum oven and analyzed for smell. The homogenous suspension was then stirred for an additional hour, added to 33 g of Ground Corn Cob and dried in a vacuum oven prior to analyzing for smell.

Smell Factor: 1

Example 23

$MgCl_2$-Mixed VFA-CMC-High Viscosity-KOH

Sodium Carboxymethyl Cellulose-High Viscosity (1.99 g, ~7.27 mmols of COOH) was dissolved in 100 mL of 2M KOH (11.11 g, 0.2 mols) over 4 hours. To this was added Isobutyric Acid (198.5 mg, 2.25 mmols), Isovaleric Acid (144.2 mg, 1.41 mmols), 2-MethylButyric Acid (187.4 mg, 1.83 mmols) and Valeric Acid (181.4 mg, 1.77 mmols) the resulting suspension was stirred for 20 minutes and to this was added Magnesium Chloride Hexahydrate (1.51 g, 7.27 mmols). The homogenous suspension was then stirred for an additional hour, added to 33 g of Ground Corn Cob and dried in a vacuum oven prior to analyzing for smell.

Smell Factor: 2

Example 24

$MgCl_2$-Mixed VFA-CMC-High Viscosity-KOH-Corn Cob

Sodium Carboxymethyl Cellulose-High Viscosity (2.05 g, ~7.27 mmols of COOH) was dissolved in 100 mL of 2M KOH (11.15 g, 0.2 mols) over 4 hours. To this was added Isobutyric Acid (198.5 mg, 2.25 mmols), Isovaleric Acid (144.2 mg, 1.41 mmols), 2-MethylButyric Acid (187.4 mg, 1.83 mmols) and Valeric Acid (181.4 mg, 1.77 mmols) the resulting suspension was stirred for 20 minutes and to this was added Magnesium Chloride Hexahydrate (1.43 g, 7.27 mmols). The homogenous suspension was then stirred for an additional hour, added to 33 g of Ground Corn Cob and dried in a vacuum oven prior to analyzing for smell.

Smell Factor: 1

Example 25

$MgCl_2$-Mixed VFA-CMC-Medium Viscosity

Sodium Carboxymethyl Cellulose-Medium Viscosity (2.03 g, ~6.36 mmols of COOH) was dissolved in 100 mL of $H_2O$ over 24 hours. To this was added Isobutyric Acid (173.7 mg, 1.97 mmols), Isovaleric Acid (126.2 mg, 1.23 mmols), 2-MethylButyric Acid (163.9 mg, 1.60 mmols) and Valeric Acid (158.7 mg, 1.55 mmols) the resulting suspension was stirred for 20 minutes and to this was added Magnesium Chloride Hexahydrate (1.29 g, 6.4 mmols). The homogenous suspension was then stirred for an additional hour, dried in the vacuum oven and analyzed for smell.

Smell Factor: 1

Example 26

$MgCl_2$-Mixed VFA-CMC-Medium Viscosity-Corn Cob

Sodium Carboxymethyl Cellulose-Medium Viscosity (2.02 g, ~6.36 mmols of COOH) was dissolved in 100 mL of $H_2O$ over 24 hours. To this was added Isobutyric Acid (173.7 mg, 1.97 mmols), Isovaleric Acid (126.2 mg, 1.23 mmols), 2-MethylButyric Acid (163.9 mg, 1.60 mmols) and Valeric Acid (158.7 mg, 1.55 mmols) the resulting suspension was stirred for 20 minutes and to this was added Magnesium Chloride Hexahydrate (1.27 g, 6.4 mmols). The homogenous suspension was then stirred for an additional hour, added to 33 g of Ground Corn Cob and dried in the vacuum oven prior to analyzing for smell.

Smell Factor: 1

Example 27

$MgCl_2$-Mixed VFA-CMC-Medium Viscosity-KOH

Sodium Carboxymethyl Cellulose-Medium Viscosity (2.00 g, ~6.36 mmols of COOH) was dissolved in 100 mL of 2M KOH (11.14 g, 0.2 mols) over 4 hours. To this was added Isobutyric Acid (173.7 mg, 1.97 mmols), Isovaleric Acid (126.2 mg, 1.23 mmols), 2-MethylButyric Acid (163.9 mg, 1.60 mmols) and Valeric Acid (158.7 mg, 1.55 mmols) the resulting suspension was stirred for 20 minutes and to this was added Magnesium Chloride Hexahydrate (1.25 g, 6.4 mmols). The homogenous suspension was then stirred for an additional hour, dried in the vacuum oven and analyzed for smell.

Smell Factor: 1

Example 28

$MgCl_2$-Mixed VFA-CMC-Medium Viscosity-KOH-Corn Cob

Sodium Carboxymethyl Cellulose-Medium Viscosity (1.98 g, ~6.36 mmols of COOH) was dissolved in 100 mL of 2M KOH (11.18 g, 0.2 mols) over 4 hours. To this was added Isobutyric Acid (173.7 mg, 1.97 mmols), Isovaleric Acid (126.2 mg, 1.23 mmols), 2-MethylButyric Acid (163.9 mg, 1.60 mmols) and Valeric Acid (158.7 mg, 1.55 mmols) the resulting suspension was stirred for 20 minutes and to this was added Magnesium Chloride Hexahydrate (1.30 g, 6.4 mmols). The homogenous suspension was then stirred for an additional hour, added to 33 g of Ground Corn Cob and dried in the vacuum oven prior to analyzing for smell.

Smell Factor: 1

Example 29

$MgCl_2$-Mixed VFA-CMC-Low Viscosity

Sodium Carboxymethyl Cellulose-Low Viscosity (4.03 g, ~10.8 mmols of COOH) was dissolved in 100 mL of $H_2O$ over 24 hours. To this was added Isobutyric Acid (295 mg, 3.35 mmols), Isovaleric Acid (214.3 mg, 2.10 mmols), 2-MethylButyric Acid (278.4 mg, 2.72 mmols) and Valeric Acid (269.6 mg, 2.63 mmols) the resulting suspension was stirred for 20 minutes and to this was added Magnesium Chloride Hexahydrate (2.20 g, 11 mmols). The homogenous suspension was then stirred for an additional hour, dried in the vacuum oven and analyzed for smell.

Smell Factor: 1

Example 30

$MgCl_2$-Mixed VFA-CMC-Low Viscosity-Corn Cob

Sodium Carboxymethyl Cellulose-Low Viscosity (3.98 g, ~10.8 mmols of COOH) was dissolved in 100 mL of $H_2O$ over 24 hours. To this was added Isobutyric Acid (295 mg, 3.35 mmols), Isovaleric Acid (214.3 mg, 2.10 mmols), 2-MethylButyric Acid (278.4 mg, 2.72 mmols) and Valeric Acid (269.6 mg, 2.63 mmols) the resulting suspension was stirred for 20 minutes and to this was added Magnesium Chloride Hexahydrate (2.15 g, 11 mmols). The homogenous suspension was then stirred for an additional hour, added to 33 g of Ground Corn Cob and dried in the vacuum oven prior to analyzing for smell.

Smell Factor: 1

Example 31

MgCl$_2$-Mixed VFA-CMC-Low Viscosity-KOH

Sodium Carboxymethyl Cellulose-Low Viscosity (4.05 g, ~10.8 mmols of COOH) was dissolved in 100 mL 2M KOH (11.19 g, 0.2 mols) over 2 hours. To this was added Isobutyric Acid (295 mg, 3.35 mmols), Isovaleric Acid (214.3 mg, 2.10 mmols), 2-MethylButyric Acid (278.4 mg, 2.72 mmols) and Valeric Acid (269.6 mg, 2.63 mmols) the resulting suspension was stirred for 20 minutes and to this was added Magnesium Chloride Hexahydrate (2.22 g, 11 mmols). The homogenous suspension was then stirred for an additional hour, dried in the vacuum oven and analyzed for smell.

Smell Factor: 1

Example 32

MgCl$_2$-Mixed VFA-CMC-Low Viscosity-KOH-Corn Cob

Sodium Carboxymethyl Cellulose-Low Viscosity (3.95 g, ~10.8 mmols of COOH) was dissolved in 100 mL 2M KOH (11.14 g, 0.2 mols) over 2 hours. To this was added Isobutyric Acid (295 mg, 3.35 mmols), Isovaleric Acid (214.3 mg, 2.10 mmols), 2-MethylButyric Acid (278.4 mg, 2.72 mmols) and Valeric Acid (269.6 mg, 2.63 mmols) the resulting suspension was stirred for 20 minutes and to this was added Magnesium Chloride Hexahydrate (2.19 g, 11 mmols). The homogenous suspension was then stirred for an additional hour, added to 33 g of Ground Corn Cob and dried in the vacuum oven prior to analyzing for smell.

Smell Factor: 1

Example 33 (Comparative)

MgCl$_2$-Mixed VFA-Alginic Acid-Corn Cob

Alginic Acid (10.01 g, 51 mmols) was dissolved in 50 mL of water and heated to 70° C. for 4 hours. To this was added Isobutyric Acid (1.39 g, 15.8 mmols), Isovaleric Acid (1.01 g, 9.89 mmols), 2-MethylButyric Acid (1.31 g, 12.9 mmols) and Valeric Acid (1.27 g, 12.4 mmols) the resulting orange/yellow suspension was stirred for 30 minutes and to this the Magnesium Chloride Hexahydrate (10.33 g, 51 mmols) was added. The homogenous suspension was stirred for an additional hour, added to 17 g of Ground Corn Cob and dried in the vacuum oven prior to analyzing for smell.

Smell Factor: 4

Example 34 (Comparative)

MgCl$_2$-Mixed VFA-Alginic Acid (Neat)

Alginic Acid (9.97 g, 51 mmols) was dissolved in 50 mL of water and heated to 70° C. for 4 hours. To this was added Isobutyric Acid (1.39 g, 15.8 mmols), Isovaleric Acid (1.01 g, 9.89 mmols), 2-MethylButyric Acid (1.31 g, 12.9 mmols) and Valeric Acid (1.27 g, 12.4 mmols) the resulting orange/yellow suspension was stirred for 30 minutes and to this the Magnesium Chloride Hexahydrate (10.38 g, 51 mmols) was added. The homogenous suspension was stirred for an additional hour dried in the vacuum oven and analyzed for smell.

Smell Factor: 5

Example 35

MgCl$_2$-Mixed VFA-Alginic Acid-KOH

Alginic Acid (9.98 g, 51 mmols) was dissolved in 50 mL of 2M KOH (5.56 g, 0.1 mols) and heated to 70° C. for 4 hours. To this was added Isobutyric Acid (1.39 g, 15.8 mmols), Isovaleric Acid (1.01 g, 9.89 mmols), 2-MethylButyric Acid (1.31 g, 12.9 mmols) and Valeric Acid (1.27 g, 12.4 mmols) the resulting orange/yellow suspension was stirred for 30 minutes and to this the Magnesium Chloride Hexahydrate (10.37 g, 51 mmols) was added. The homogenous suspension was stirred for an additional hour dried in the vacuum oven and analyzed for smell.

Smell Factor: 1

Example 36

MgCl$_2$-Mixed VFA-Alginic Acid-KOH-Corn Cob

Alginic Acid (9.95 g, 51 mmols) was dissolved in 50 mL 2M KOH (5.56 g, 0.1 mols) and heated to 70° C. for 4 hours. To this was added Isobutyric Acid (1.42 g, 15.8 mmols), Isovaleric Acid (1.01 g, 9.89 mmols), 2-MethylButyric Acid (1.31 g, 12.9 mmols) and Valeric Acid (1.26 g, 12.4 mmols) the resulting orange/yellow suspension was stirred for 30 minutes and to this the Magnesium Chloride Hexahydrate (10.33 g, 51 mmols) was added. The homogenous suspension was stirred for an additional hour, added to 17 g of Ground Corn Cob and dried in the vacuum oven prior to analyzing for smell.

Smell Factor: 2

Example 37 (Comparative)

MgCl$_2$-Mixed VFA-Polyacrylic Acid

Polyacrylic Acid (50% solution, 7.60 g, 51 mmols), was dissolved in 50 mL of water. Isobutyric Acid (1.39 g, 15.8 mmols), Isovaleric Acid (1.01 g, 9.89 mmols), 2-MethylButyric Acid (1.32 g, 12.9 mmols) and Valeric Acid (1.25 g, 12.4 mmols) were added which was followed by the dropwise addition of Magnesium Chloride Hexahydrate (10.40 g, 51 mmol) dissolved in 5 mL of water. The resulting white suspension was stirred for an additional hour until homogenous, dried in a vacuum oven and analyzed for smell.

Smell Factor: 7

Example 38 (Comparative)

MgCl$_2$-Mixed VFA-Polyacrylic Acid-Corn Cob

Polyacrylic Acid (50% solution, 7.57 g, 51 mmols), was dissolved in 50 mL of water. Isobutyric Acid (1.40 g, 15.8 mmols), Isovaleric Acid (1.01 g, 9.89 mmols), 2-MethylButyric Acid (1.31 g, 12.9 mmols) and Valeric Acid (1.22 g, 12.4 mmols) were added which was followed by the dropwise addition of Magnesium Chloride Hexahydrate (10.36 g, 51 mmol) dissolved in 5 mL of water. The resulting white suspension was stirred for an additional hour until homogenous, added to 17 g of Ground Corn Cob and dried in the vacuum oven prior to smell analysis.

Smell Factor: 6

Example 39

MgCl$_2$-Mixed VFA-Polyacrylic Acid-KOH

Polyacrylic Acid (50% solution, 7.50 g, 51 mmols), was dissolved in 50 mL of 2M KOH (5.54 g, 0.1 mols). Isobutyric Acid (1.39 g, 15.8 mmols), Isovaleric Acid (0.99 g, 9.89 mmols), 2-MethylButyric Acid (1.31 g, 12.9 mmols) and Valeric Acid (1.21 g, 12.4 mmols) were added which was followed by the dropwise addition of Magnesium Chloride Hexahydrate (10.34 g, 51 mmol) dissolved in 5 mL of water. The resulting white suspension was stirred for an additional hour until homogenous, dried in a vacuum oven and analyzed for smell.

Smell Factor: 3

Example 40

$MgCl_2$-Mixed VFA-Polyacrylic Acid-KOH-Corn Cob

Polyacrylic Acid (50% solution, 7.55 g, 51 mmols), was dissolved in 50 mL of 2M KOH (5.59 g, 0.1 mols). Isobutyric Acid (1.33 g, 15.8 mmols), Isovaleric Acid (1.01 g, 9.89 mmols), 2-MethylButyric Acid (1.31 g, 12.9 mmols) and Valeric Acid (1.27 g, 12.4 mmols) were added which was followed by the dropwise addition of Magnesium Chloride Hexahydrate (10.31 g, 51 mmol) dissolved in 5 mL of water. The resulting white suspension was stirred for an additional hour until homogenous, added to 17 g of Ground Corn Cob and dried in the vacuum oven prior to smell analysis.

Smell Factor: 2

Example 41

$MgCl_2$-Mixed VFA-Pectin-KOH

Pectin (10.04 g, 51 mmols), was suspended in 50 mL of 4M KOH (11.12 g, 0.2 mols) and heated to 70° C. for 4 hours. Isobutyric Acid (1.39 g, 15.8 mmols), Isovaleric Acid (1.00 g, 9.89 mmols), 2-MethylButyric Acid (1.30 g, 12.9 mmols) and Valeric Acid (1.30 g, 12.4 mmols) were added in one portion and after 10 minutes of stirring Magnesium Chloride Hexahydrate (10.36 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 2

Example 42

$MgCl_2$-Mixed VFA-Pectin-KOH-Ground Corn Cob

Pectin (9.94 g, 51 mmols), was suspended in 50 mL of 4M KOH (11.19 g, 0.2 mols) and heated to 70° C. for 4 hours. Isobutyric Acid (1.38 g, 15.8 mmols), Isovaleric Acid (0.98 g, 9.89 mmols), 2-MethylButyric Acid (1.31 g, 12.9 mmols) and Valeric Acid (1.21 g, 12.4 mmols) were added in one portion and after 10 minutes of stirring Magnesium Chloride Hexahydrate (10.36 g, 51 mmols) in 5 mL of water was slowly added to the resulting reddish orange suspension. After stirring for an additional hour to ensure homogeneity the burnt red suspension was added to 17 g of Ground Corn Cob and dried in a vacuum oven prior to smell analysis.

Smell Factor: 1

Example 43

$MgCl_2$-Mixed VFA-Pectin-KOH-Ground Corn

Pectin (10.00 g, 51 mmols), was suspended in 50 mL of 4M KOH (11.15 g, 0.2 mols) and heated to 70° C. for 4 hours. Isobutyric Acid (1.38 g, 15.8 mmols), Isovaleric Acid (1.00 g, 9.89 mmols), 2-MethylButyric Acid (1.28 g, 12.9 mmols) and Valeric Acid (1.27 g, 12.4 mmols) were added in one portion and after 10 minutes of stirring Magnesium Chloride Hexahydrate (10.36 g, 51 mmols) in 5 mL of water was slowly added to the resulting reddish orange suspension. After stirring for an additional hour to ensure homogeneity the burnt red suspension was added to 17 g of Ground Corn and dried in a vacuum oven prior to smell analysis.

Smell Factor: 1

Example 44

$MgCl_2$-Mixed VFA-Pectin-KOH-Cellulose

Pectin (9.91 g, 51 mmols), was suspended in 50 mL of 4M KOH (11.18 g, 0.2 mols) and heated to 70° C. for 4 hours. Isobutyric Acid (1.40 g, 15.8 mmols), Isovaleric Acid (0.97 g, 9.89 mmols), 2-MethylButyric Acid (1.31 g, 12.9 mmols) and Valeric Acid (1.25 g, 12.4 mmols) were added in one portion and after 10 minutes of stirring Magnesium Chloride Hexahydrate (10.36 g, 51 mmols) in 5 mL of water was slowly added to the resulting reddish orange suspension. After stirring for an additional hour to ensure homogeneity the burnt red suspension was added to 17 g of Cellulose and dried in a vacuum oven prior to smell analysis.

Smell Factor: 1

Example 45

$MgCl_2$-Mixed VFA-Pectin-KOH-Rice Flour

Pectin (9.99 g, 51 mmols), was suspended in 50 mL of 4M KOH (11.10 g, 0.2 mols) and heated to 70° C. for 4 hours. Isobutyric Acid (1.39 g, 15.8 mmols), Isovaleric Acid (1.01 g, 9.89 mmols), 2-MethylButyric Acid (1.27 g, 12.9 mmols) and Valeric Acid (1.27 g, 12.4 mmols) were added in one portion and after 10 minutes of stirring Magnesium Chloride Hexahydrate (10.31 g, 51 mmols) in 5 mL of water was slowly added to the resulting reddish orange suspension. After stirring for an additional hour to ensure homogeneity the burnt red suspension was added to 17 g of Rice Flour and dried in a vacuum oven prior to smell analysis.

Smell Factor: 1

Example 46 (Comparative)

Ammonia VFA (1:1, Neat)

Potassium Hydroxide (2.96 g, 52 mmols) was dissolved in 50 mL of water. To this was added Isobutyric Acid (1.39 g, 15.8 mmols), Isovaleric Acid (1.01 g, 9.89 mmols), 2-MethylButyric Acid (1.31 g, 12.9 mmols) and Valeric Acid (1.27 g, 12.4 mmols) in one portion with an additional stirring for 10 minutes at room temperature. Ammonium Chloride Hexahydrate (2.78 g, 52 mmols) was dissolved in 5 mL of water and added slowly to the reaction flask. The white suspension was stirred for 30 minutes, dried in a vacuum oven and analyzed for smell.

Smell Factor: 8

Example 47 (Comparative)

K-VFA (1:1, Neat)

Potassium Hydroxide (2.95 g, 52 mmols) was dissolved in 50 mL of water. To this was added Isobutyric Acid (1.39 g, 15.8 mmols), Isovaleric Acid (0.99 g, 9.89 mmols), 2-MethylButyric Acid (1.31 g, 12.9 mmols) and Valeric Acid (1.27 g, 12.4 mmols) in one portion with an additional stirring for 10 minutes at room temperature. The white suspension was dried in a vacuum oven and analyzed for smell.

Smell Factor: 4

Example 48 (Comparative)

Na-VFA (1:1, Neat)

Sodium Hydroxide (2.10 g, 52 mmols) was dissolved in 50 mL of water. To this was added Isobutyric Acid (1.33 g, 15.8 mmols), Isovaleric Acid (1.00 g, 9.89 mmols), 2-MethylButyric Acid (1.29 g, 12.9 mmols) and Valeric Acid (1.27 g, 12.4 mmols) in one portion with an additional stirring for 10 minutes at room temperature. The white suspension was dried in a vacuum oven and analyzed for smell.

Smell Factor: 4

Example 49

$CaCl_2$-Isobutyric-CMC High Viscosity-KOH

Sodium Carboxymethyl Cellulose-High Viscosity (2.03 g, ~7.27 mmols of COOH) was dissolved in 100 mL of 2M KOH (11.21 g, 0.2 mols) over 4 hours. To this was added Isobutyric Acid (0.67 mL, 7.27 mmols) the resulting suspension was stirred for 20 minutes and to this was added Calcium Chloride Dihydrate (1.06 g, 7.27 mmols). The homogenous suspension was then stirred for an additional hour and dried in a vacuum oven prior to analyzing for smell.

Smell Factor: 1

Example 50

$MgCl_2$-Valeric/Isovaleric-CMC High Viscosity-NaOH

Sodium Carboxymethyl Cellulose-High Viscosity (2.00 g, ~7.27 mmols of COOH) was dissolved in 100 mL of 2M NaOH (7.95 g, 0.2 mols) over 4 hours. Valeric Acid (0.39 mL, 3.6 mmols) and Isovaleric acid (0.40 mL, 3.6 mmols) were added to the suspension which was stirred for 20 minutes and to this was added Magnesium Chloride Hexahydrate (1.44 g, 7.27 mmols). The homogenous suspension was then stirred for an additional hour and dried in a vacuum oven prior to analyzing for smell.

Smell Factor: 1

Example 51

$CaCl_2$-Isobutyric/Valeric-Alginic-KOH

Alginic Acid (10.01 g, 51 mmols) was dissolved in 100 mL of 2M KOH (11.12 g, 0.2 mols) and heated to 70° C. for 4 hours. To this was added Isobutyric Acid (2.37 g, 25.5 mmols) and Valeric Acid (2.78 mL, 25.5 mmols) the resulting orange/yellow suspension was stirred for 30 minutes and to this the Calcium Chloride Dihydrate (7.50 g, 51 mmols) was added. The homogenous suspension was stirred for an additional hour dried in the vacuum oven and analyzed for smell.

Smell Factor: 1

Example 52

$MgCl_2$-Isobutyric/Valeric/Isovaleric-Alginic-NaOH

Alginic Acid (9.93 g, 51 mmols) was dissolved in 100 mL of 2M NaOH (8.05 g, 0.2 mols) and heated to 70° C. for 4 hours. To this was added Isobutyric (1.58 mL, 17 mmols), Valeric Acid (1.86 mL, 17 mmols) and Isovaleric Acid (1.87 mL, 17 mmols) the resulting orange/yellow suspension was stirred for 30 minutes and to this the Magnesium Chloride Hexahydrate (10.33 g, 51 mmols) was added. The homogenous suspension was stirred for an additional hour dried in the vacuum oven and analyzed for smell.

Smell Factor: 2

Example 53

$CaCl_2$-Valeric/Isovaleric/2-Methyl-Butyric-Pectin-KOH

Pectin (10.12 g, 51 mmols), was suspended in 100 mL of 2M KOH (11.15 g, 0.2 mols) and heated to 70° C. for 4 hours. Valeric Acid (1.86 mL, 17 mmols), Isovaleric Acid (1.87 mL, 17 mmols) and 2-MethylButyric Acid (1.88 mL, 17 mmols) were added in one portion and after 10 minutes of stirring Calcium Chloride Dihydrate (7.49 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 1

Example 54

$MgCl_2$-VFA Mix-Pectin-NaOH

Pectin (9.97 g, 51 mmols), was suspended in 100 mL of 2M NaOH (8.11 g, 0.2 mols) and heated to 70° C. for 4 hours. Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added in one portion and after 10 minutes of stirring Magnesium Chloride Hexahydrate (10.35 g, 51 mmols) in 5 mL of water was slowly added to the resulting reddish orange suspension. After stirring for an additional hour to ensure homogeneity the burnt red suspension was dried in a vacuum oven and analyzed for smell.

Smell Factor: 1

Example 55

$Ca(OH)_2$-Isobutyric-Pectin-KOH

Pectin (10.00 g, 51 mmols), was suspended in 100 mL of 1M KOH (5.60 g, 0.1 mols) and heated to 70° C. for 4 hours. Isobutyric Acid (4.73 mL, 51 mmols) was added in one portion and after 10 minutes of stirring Calcium Hydroxide (3.78 g, 51 mmols) was added to the resulting reddish orange suspension. After stirring for an additional hour to ensure homogeneity the burnt red suspension was dried in a vacuum oven and analyzed for smell.

Smell Factor: 1

Example 56

$Mg(OH)_2$-Isobutyric/2-Methyl-Butyric-Pectin-KOH

Pectin (10.11 g, 51 mmols), was suspended in 100 mL of 1M KOH (5.55 g, 0.1 mols) and heated to 70° C. for 4 hours. Isobutyric Acid (2.37 mL, 25.5 mmols) and 2-Methyl Butyric Acid (2.82 mL, 25.5 mmols) were added in one portion and after 10 minutes of stirring Magnesium Hydroxide (2.98 g, 51 mmols) was added to the resulting reddish orange suspension. After stirring for an additional hour to ensure homogeneity the burnt red suspension was dried in a vacuum oven and analyzed for smell.

Smell Factor: 1

Example 57

$CaCl_2$-VFA Mix-Polyacrylic Acid-KOH

Polyacrylic Acid (50% solution, 7.54 g, 51 mmols), was dissolved in 100 mL of 2M KOH (11.20 g, 0.2 mols). Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added and subsequently followed by the addition of Calcium Chloride Dihydrate (7.49 g, 51 mmol) dissolved in 5 mL of water. The resulting white suspension was stirred for an additional hour until homogenous, dried in a vacuum oven and analyzed for smell.

Smell Factor: 1

Example 58

$MgCl_2$-Valeric-Polyacrylic Acid-NaOH

Polyacrylic Acid (50% solution, 7.48 g, 51 mmols), was dissolved in 100 mL of 2M NaOH (7.98 g, 0.2 mols). Valeric Acid (5.57 mL, 51 mmols) was added to the clear solution and followed by the drop wise addition of Magnesium Chloride Hexahydrate (10.29 g, 51 mmol) dissolved in 5 mL of water. The resulting white suspension was stirred for an additional hour until homogenous, dried in a vacuum oven and analyzed for smell.

Smell Factor: 1

Example 59 (Comparative)

$MgCl_2$-VFA Mix-Tartaric Acid-KOH

Tartaric acid (7.66 g, 51 mmols) was dissolved in 100 mL of water to which was slowly added KOH (11.2 g, 0.2 mols). After stirring for 20 minutes, Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added to the clear solution. When the solution clarifies Magnesium Chloride Hexahydrate (10.37 g, 51 mmols) is added and subsequently a fine white precipitant forms. The white suspension was stirred for an additional hour until homogenous, dried in a vacuum oven and analyzed for smell.

Smell Factor: 7

Example 60 (Comparative)

$MgCl_2$-VFA Mix-Citric Acid-KOH

Citric acid monohydrate (10.7 g, 51 mmols) was dissolved in 100 mL of water to which was slowly added KOH (11.2 g, 0.2 mols). After stirring for 20 minutes, Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added to the clear solution. When the solution clarifies Magnesium Chloride Hexahydrate (10.35 g, 51 mmols) is added. The colorless solution was stirred for an additional hour until homogenous, dried in a vacuum oven and analyzed for smell.

Smell Factor: 6

Example 61 (Comparative)

$NH_4Cl$-VFA Mix-KOH-Liquid

Potassium Hydroxide (2.99 g, 52 mmols) was dissolved in 100 mL of water. To this was added Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) in one portion with an additional stirring for 10 minutes at room temperature. Ammonium Chloride (2.77 g, 52 mmols) was dissolved in 5 mL of water and added slowly to the reaction flask. The white suspension was stirred for 30 minutes and then analyzed for smell while still a liquid.

Smell Factor: 4

Example 62 (Comparative)

VFA Mix-Liquid

Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were dissolved in 100 mL of water and stirred for 10 minutes to ensure homogeneity. The colorless solution was then analyzed for smell while still a liquid.

Smell Factor: 6

Example 63

$MgCl_2$-VFA Mix-Pectin-KOH-Liquid

Pectin (10 g, 51 mmols), was suspended in 100 mL of 2M KOH (11.13 g, 0.2 mols) and heated to 70° C. for 4 hours. Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added in one portion and after 10 minutes of stirring Magnesium Chloride Hexahydrate (10.36 g, 51 mmols) in 5 mL of water was slowly added to the resulting reddish orange suspension. After stirring for an additional hour to ensure homogeneity the burnt red suspension was then analyzed for smell while it was still a liquid.

Smell Factor: 1

Example 64

$ZnCl_2$-Isobutyric-CMC-KOH

Sodium Carboxymethyl Cellulose-High Viscosity (1.99 g, ~7.27 mmols of COOH) was dissolved in 100 mL of 2M KOH (11.24 g, 0.2 mols) over 4 hours. To this was added Isobutyric Acid (0.67 mL, 7.27 mmols) the resulting suspension was stirred for 20 minutes and to this was added Zinc Chloride (0.99 g, 7.27 mmols). The homogenous suspension was then stirred for an additional hour and dried in a vacuum oven prior to analyzing for smell.

Smell Factor: 1

Example 65

$CuCl_2$-Isobutyric/Valeric-Alginic-NaOH

Alginic Acid (9.96 g, 51 mmols) was dissolved in 100 mL of 2M NaOH (8.01 g, 0.2 mols) and heated to 70° C. for 4 hours. To this was added Isobutyric Acid (2.37 g, 25.5 mmols) and Valeric Acid (2.78 mL, 25.5 mmols) the resulting orange/yellow suspension was stirred for 30 minutes and to this the Copper Chloride dihydrate (8.71 g, 51 mmols) was added. The homogenous suspension was stirred for an additional hour dried in the vacuum oven and analyzed for smell.

Smell Factor: 1

Example 66

$MnCl_2$-Valeric/Isovaleric/2-Methyl-Butyric-Pectin-KOH

Pectin (10.03 g, 51 mmols), was suspended in 100 mL of 2M KOH (11.26 g, 0.2 mols) and heated to 70° C. for 4 hours. Valeric Acid (1.86 mL, 17 mmols), Isovaleric Acid (1.87 mL, 17 mmols) and 2-MethylButyric Acid (1.88 mL, 17 mmols) were added in one portion and after 10 minutes of stirring Manganese Chloride (6.41 g, 51 mmol) was slowly added to the resulting red/orange suspension. After stirring for an additional hour to ensure homogeneity the burnt red suspension was dried in a vacuum oven and analyzed for smell.

Smell Factor: 1

Example 67

FeCl$_2$-VFA Mix-PAA-NaOH

Polyacrylic Acid (50% solution, 7.50 g, 51 mmols), was dissolved in 100 mL of 2M NaOH (8.09 g, 0.2 mols). Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added and subsequently followed by the addition of Ferrous Chloride tetrahydrate (10.16 g, 51 mmol). The resulting green/brown suspension was stirred for an additional hour until homogenous, dried in a vacuum oven and analyzed for smell.

Smell Factor: 1

Example 68

ZnCl$_2$-Isobutyric-CMC-KOH-Liquid

Sodium Carboxymethyl Cellulose-High Viscosity (1.97 g, ~7.27 mmols of COOH) was dissolved in 100 mL of 2M KOH (11.2 g, 0.2 mols) over 4 hours. To this was added Isobutyric Acid (0.67 mL, 7.27 mmols) the resulting suspension was stirred for 20 minutes and to this was added Zinc Chloride (0.99 g, 7.27 mmols). The homogenous suspension was then stirred for an additional hour and analyzed for smell while still a liquid.

Smell Factor: 1

Example 69

CuCl$_2$-Isobutyric/Valeric-Alginic-NaOH-Liquid

Alginic Acid (10.06 g, 51 mmols) was dissolved in 100 mL of 2M NaOH (8.03 g, 0.2 mols) and heated to 70° C. for 4 hours. To this was added Isobutyric Acid (2.37 g, 25.5 mmols) and Valeric Acid (2.78 mL, 25.5 mmols) the resulting orange/yellow suspension was stirred for 30 minutes and to this the Copper Chloride dihydrate (8.72 g, 51 mmols) was added. The homogenous suspension was stirred for an additional hour and analyzed for smell while still a liquid.

Smell Factor: 1

Example 70

MnCl$_2$-Valeric/Isovaleric/2-Methyl-Butyric-Pectin-KOH-Liquid

Pectin (9.90 g, 51 mmols), was suspended in 100 mL of 2M KOH (11.22 g, 0.2 mols) and heated to 70° C. for 4 hours. Valeric Acid (1.86 mL, 17 mmols), Isovaleric Acid (1.87 mL, 17 mmols) and 2-MethylButyric Acid (1.88 mL, 17 mmols) were added in one portion and after 10 minutes of stirring Manganese Chloride (6.42 g, 51 mmol) was slowly added to the resulting red/orange suspension. After stirring for an additional hour to ensure homogeneity the burnt red suspension was analyzed for smell while still a liquid.

Smell Factor: 1

Example 71

FeCl$_2$-VFA Mix-PAA-NaOH-Liquid

Polyacrylic Acid (50% solution, 7.59 g, 51 mmols), was dissolved in 100 mL of 2M NaOH (8.03 g, 0.2 mols). Isobutyric Acid (1.46 mL, 15.8 mmols), Valeric Acid (1.36 mL, 12.4 mmols), Isovaleric Acid (1.09 mL, 9.89 mmols) and 2-MethylButyric Acid (1.41 mL, 12.9 mmols) were added and subsequently followed by the addition of Ferrous Chloride tetrahydrate (10.14 g, 51 mmol). The resulting green/brown suspension was stirred for an additional hour until homogenous and then analyzed for smell while still a liquid.

Smell Factor: 1

Butyric Acid Examples

Example 72

ZnCl$_2$-Butyric-CMC-NaOH

Sodium Carboxymethyl Cellulose-High Viscosity (2.02 g, ~7.27 mmols of COOH) was dissolved in 100 mL of 2M NaOH (8 g, 0.2 mols) over 4 hours. To this was added Butyric Acid (0.61 mL, 7.27 mmols) the resulting suspension was stirred for 20 minutes and to this was added Zinc Chloride (0.99 g, 7.27 mmols). The homogenous suspension was then stirred for an additional hour and dried in a vacuum oven prior to analyzing for smell.

Smell Factor: 1

Example 73

CuCl$_2$-Butyric-Alginic-KOH

Alginic Acid (9.97 g, 51 mmols) was dissolved in 100 mL of 2M KOH (11.18 g, 0.2 mols) and heated to 70° C. for 4 hours. To this was added Butyric Acid (4.68 mL, 51 mmols) the resulting orange/yellow suspension was stirred for 30 minutes and to this the Copper Chloride dihydrate (8.70 g, 51 mmols) was added. The homogenous suspension was stirred for an additional hour dried in the vacuum oven and analyzed for smell.

Smell Factor: 2

Example 74

MgCl$_2$-Butyric-Pectin-KOH

Pectin (10.05 g, 51 mmols), was suspended in 100 mL of 2M KOH (11.21 g, 0.2 mols) and heated to 70° C. for 4 hours. Butyric Acid (4.68 mL, 51 mmols) was added in one portion and after 10 minutes of stirring Magnesium Chloride Hexahydrate (10.38 g, 51 mmol) was slowly added to the resulting red/orange suspension. After stirring for an additional hour to ensure homogeneity the burnt red suspension was dried in a vacuum oven and analyzed for smell.

Smell Factor: 1

Example 75

CaCl$_2$-Butyric-Pectin-KOH

Pectin (10.11 g, 51 mmols), was suspended in 100 mL of 2M KOH (11.18 g, 0.2 mols) and heated to 70° C. for 4 hours. Butyric Acid (4.68 mL, 51 mmols) was added in one portion and after 10 minutes of stirring Calcium Chloride dihydrate (7.51 g, 51 mmol) was slowly added to the resulting red/orange suspension. After stirring for an additional hour to ensure homogeneity the burnt red suspension was dried in a vacuum oven and analyzed for smell.

Smell Factor: 1

Example 76

MnCl$_2$-Butyric-PAA-NaOH

Polyacrylic Acid (50% solution, 7.58 g, 51 mmols), was dissolved in 100 mL of 2M NaOH (8.02 g, 0.2 mols). Butyric Acid (4.68 mL, 51 mmols) was added and subsequently followed by the addition of Manganese Chloride (6.41 g, 51 mmol). The resulting green/brown suspension was stirred for an additional hour until homogenous, dried in a vacuum oven and analyzed for smell.
Smell Factor: 2

Example 77

ZnCl$_2$-Butyric-CMC-NaOH-Liquid

Sodium Carboxymethyl Cellulose-High Viscosity (1.98 g, ~7.27 mmols of COOH) was dissolved in 100 mL of 2M NaOH (7.95 g, 0.2 mols) over 4 hours. To this was added Butyric Acid (0.61 mL, 7.27 mmols) the resulting suspension was stirred for 20 minutes and to this was added Zinc Chloride (1.00 g, 7.27 mmols). The homogenous suspension was then stirred for an additional hour and then analyzed for smell while still a liquid.
Smell Factor: 1

Example 78

MgCl$_2$-Butyric-Pectin-KOH-Liquid

Pectin (10.04 g, 51 mmols), was suspended in 100 mL of 2M KOH (11.16 g, 0.2 mols) and heated to 70° C. for 4 hours. Butyric Acid (4.68 mL, 51 mmols) was added in one portion and after 10 minutes of stirring Magnesium Chloride Hexahydrate (10.37 g, 51 mmol) was slowly added to the resulting red/orange suspension. After stirring for an additional hour to ensure homogeneity the burnt red suspension was analyzed for smell while still a liquid.
Smell Factor: 2

Example 79

CaCl$_2$-Butyric-Pectin-KOH-Liquid

Pectin (10.01 g, 51 mmols), was suspended in 100 mL of 2M KOH (11.23 g, 0.2 mols) and heated to 70° C. for 4 hours. Butyric Acid (4.68 mL, 51 mmols) was added in one portion and after 10 minutes of stirring Calcium Chloride dihydrate (7.54 g, 51 mmol) was slowly added to the resulting red/orange suspension. After stirring for an additional hour to ensure homogeneity the burnt red suspension was analyzed for smell while still a liquid.
Smell Factor: 2

Example 80

MnCl$_2$-Butyric-PAA-NaOH-Liquid

Polyacrylic Acid (50% solution, 7.57 g, 51 mmols), was dissolved in 100 mL of 2M NaOH (7.99 g, 0.2 mols). Butyric Acid (4.68 mL, 51 mmols) was added and subsequently followed by the addition of Manganese Chloride (6.41 g, 51 mmol). The resulting pink suspension was stirred for an additional hour until homogenous and then analyzed for smell while still a liquid.
Smell Factor: 2

Example 81 (Determination of Effect on Milk Production)

The purpose of this example was to determine the response of early lactation dairy cattle to the compound of Example 1 (with no carrier) as indicated by increased production of milk and milk components. 38 cows were selected, 19 in a controlled group, and 19 to be fed the product of Example 1. All animals were fed the same feed with the only difference being whether or not product of Example 1 was fed.

Composition of a robot fed pellet with rumen product of Example 1 was as follows:
- Ground corn, 25.5%
- Aminoplus (treated soybean meal), 23.25%
- Corn gluten feed, 17.75%
- Wheat mids, 11.7%
- Rumen product of Example 1, 10%
- Soybean meal, 4.6%
- Molasses, 3.93%
- Rumen inert fat, 2.75%
- MetaSmart, 0.52%

Listed in Tables 1 and 2 are the typical ingredient profile of the bunk mix and the combined bunk mix and robot pellet. Ingredient composition of the diet of course will vary from cow to cow as the amount of pellets offered to each cow vary by the level of milk production and days in milk. Feedstuffs were analyzed for nutrient content prior to the start of the study.

TABLE 1

Ingredient composition of bunk mix for lactating cows[a].

| Ingredient, % of dry matter | Lactating Diet |
| --- | --- |
| Corn silage | 30.14 |
| Alfalfa silage | 34.45 |
| Wheat straw | 1.86 |
| Corn grain, ground high moisture | 10.99 |
| Partially mixed ration (PMR) Base | 6.77 |
| Soybean meal, solvent extracted, 48% CP | 5.96 |
| Ecker mix | 9.82 |

[a]Diets fed ad libitum.

Table 2 shows a typical composition of the diet (PMR plus robot fed pellet).

| Ingredient, % of dry matter | Control Diet | Treatment Diet |
| --- | --- | --- |
| Corn silage | 27.50 | 27.50 |
| Alfalfa silage | 20.39 | 20.39 |
| Alfalfa hay | 7.02 | 7.02 |
| Wheat straw | 1.60 | 1.60 |
| Corn grain, fine ground | 8.22 | 7.64 |
| Corn grain, high moisture, medium grind | 9.85 | 9.85 |
| Amino Plus ®[a] | 6.13 | 6.03 |
| Wheat mids | 5.39 | 4.79 |
| Soybean hulls | 4.70 | 4.70 |
| Corn gluten feed, dry | 3.19 | 3.18 |
| Soybean meal, solvent | 1.49 | 2.04 |
| Energy Booster ®[b] | 1.00 | 1.05 |
| Alfalfa meal, dehydrated | 0.89 | — |
| Isoacid product of Example 1 | — | 1.68 |
| Molasses | 0.65 | 0.58 |
| Sodium bicarbonate | 0.51 | 0.51 |
| Salt | 0.36 | 0.36 |
| Tallow, porcine | 0.29 | 0.29 |
| Trace minerals, vitamins, mycotoxin binder | 0.19 | 0.19 |
| MetaSmart ®[c] | 0.18 | 0.18 |
| AjiPro L ®[d] | 0.15 | 0.15 |
| Magnesium oxide | 0.14 | 0.14 |
| Calcium carbonate | 0.09 | 0.09 |
| Dicalcium phosphate | 0.01 | 0.01 |
| Amaferm ®[e] | 0.03 | 0.03 |

[a]Ag Processing, Inc., Omaha, NE USA
[b]Milk Specialties Global, Eden Prairie, MN USA
[c]Adessio, Commentry, France
[d]Ajinomoto North America, Inc., Raleigh, NC 27610
[e]Biozyme Inc., St. Joseph, MO USA Treatments were delivered to cows and robot milkers by a pelleted grain mix. Eating times were once a day as determined by farm staff, with diets fed ad libitum. Feed refusals were removed once a day just prior to fresh feed delivery. Stalls were raked throughout the day as needed to remove feces and urine deposited on stall platforms.

Table 3 shows the effect of treatment on body weight and lactation performance of 19 cows assigned to the study.

TABLE 3

| Item | Control | Rumen product | SEM | P-value |
|---|---|---|---|---|
| Cows, n | 19 | 19 | | |
| Parity[a] | 2.7 (1.1) | 3.1 (1.2) | | |
| Days in milk at start of study[a] | 60.1 (24.4) | 60.2 (24.8) | | |
| Milk, lb/d | 112.5 | 114.7 | 2.6 | 0.38 |
| Energy-corrected milk[b], lb/d | 108.7 | 112.5 | 2.3 | 0.11 |
| Fat, lb/d | 3.71 | 3.91 | 0.08 | 0.01 |
| Protein, lb/d | 3.31 | 3.36 | 0.08 | 0.57 |
| Fat, % | 3.31 | 3.44 | 0.05 | 0.02 |
| Protein, % | 2.95 | 2.94 | 0.03 | 0.63 |
| Body weight, final, lb | 1584 | 1570 | 25 | 0.58 |

[a]3.5% fat and 3.0% true protein

Data was statistically analyzed using a model that included a covariate (average of the respective variable the week before cows started to receive their respective treatments) and treatment.

It should be noted that there was a slight bridging issue with pellets for the cows fed the pellet with the rumen product of Example 1 such that from time to time, some cows would not receive the recommended amount of pellets.

In this study, one control cow developed mastitis and was removed from the study. To keep the study balanced, the rumen product of Example 1 cow that was paired with the control cow that was removed from the study, was removed from the study as well.

Overall, cows fed the pellet with the rumen product of Example 1 produced more milk fat (P≤0.05) and tended to produced more energy corrected milk (P≤0.15). Increased milk fat production was the result of cows fed the rumen product diet producing milk with a higher fat content (P≤0.05).

Results of this study indicate that feeding the rumen product of Example 1 to dairy cattle increases fat production and tends to increase production of energy-corrected milk. It should be noted that production response to the rumen product of Example 1 may have been limited due to cows not receiving their full allotment of treatment pellets. Even so, the increase in milk production was statistically significant.

As can be seen, the volatile fatty acid effect on milk production in terms of enhancing it occurs with the non-smelly product of the present invention, indicating operability and proof of effectiveness for its intended use.

What is claimed is:

1. A feed supplement energy source for ruminants, swine, and poultry comprising: a feed supplement energy source carrier; and
   a reaction product obtained by reacting a pendent carboxylic acid group on a water soluble polycarboxylic acid, a polyvalent metal salt, and a C3-C10 fatty acid, whereby the polyvalent metal ion is bonded to the pendant carboxylic acid group of the polycarboxylic acid and the carboxylic acid group of the C3-C10 fatty acid, wherein the polycarboxylic acid with pendant carboxylic groups is selected from the group consisting of pectin, alginic acid and carboxymethylcellulose.

2. The feed supplement of claim 1 wherein the fatty acid is an isoacid selected from the group consisting of isobutyric, isovaleric, 2-methyl-butyric and valeric acids.

3. The feed supplement of claim 1 wherein the metal of the metal salt is selected from calcium, magnesium, zinc, manganese, copper and iron.

4. The feed supplement of claim 1 which is dried.

5. The feed supplement of claim 1 wherein the feed supplement carrier is selected from the group consisting of corn cobs, whey, fermentation by-products, soybean flour and meal, and barley.

6. The feed supplement of claim 1 in liquid format.

* * * * *

UNITED STATES PATENT AND TRADEMARK OFFICE
CERTIFICATE OF CORRECTION

PATENT NO.        : 10,034,946 B2
APPLICATION NO.   : 14/805571
DATED             : July 31, 2018
INVENTOR(S)       : Peter A. Stark, Cory Shawn Kending and Michael Thomas Socha Page 1 of 1

It is certified that error appears in the above-identified patent and that said Letters Patent is hereby corrected as shown below:

In the Claims

<u>In Column 24, Claim 1, Lines 15-17:</u>
DELETE "A feed supplement energy source for ruminants, swine, and poultry comprising: a feed supplement energy source carrier; and"
INSERT --A feed supplement for ruminants useful to increase milk production comprising: a feed supplement carrier; and--

Signed and Sealed this
Sixteenth Day of October, 2018

Andrei Iancu
*Director of the United States Patent and Trademark Office*